US012793858B2

(12) United States Patent
P R et al.

(10) Patent No.: US 12,793,858 B2
(45) Date of Patent: Nov. 10, 2026

(54) METHOD AND SYSTEM FOR RISK PREDICTION OF NEONATAL INFECTION

(71) Applicant: NEMOCARE WELLNESS PRIVATE LIMITED, Hyderabad (IN)

(72) Inventors: Manoj Sanker P R, Bangalore Karnataka (IN); Sabari Prabaaker R, Tamil Nadu Trichy (IN)

( * ) Notice: Subject to any disclaimer, the term of this patent is extended or adjusted under 35 U.S.C. 154(b) by 291 days.

(21) Appl. No.: 18/566,039

(22) PCT Filed: May 31, 2022

(86) PCT No.: PCT/IN2022/050505
§ 371 (c)(1),
(2) Date: Nov. 30, 2023

(87) PCT Pub. No.: WO2022/254460
PCT Pub. Date: Dec. 8, 2022

(65) Prior Publication Data

US 2024/0274294 A1 Aug. 15, 2024

(30) Foreign Application Priority Data

May 31, 2021 (IN) ............................. 202141004156

(51) Int. Cl.
*G16H 50/30* (2018.01)
*A61B 5/00* (2006.01)
(Continued)

(52) U.S. Cl.
CPC ........... *G16H 50/30* (2018.01); *A61B 5/0205* (2013.01); *A61B 5/7267* (2013.01);
(Continued)

(58) Field of Classification Search
CPC ........ G16H 50/30; G16H 40/67; G16H 20/10; G16H 50/50; A61B 5/0205; A61B 5/7267;
(Continued)

(56) References Cited

U.S. PATENT DOCUMENTS 12,176,111 B2 * 12/2024 Fornwalt ................ G06N 20/00
2025/0166840 A1 * 5/2025 Zhang .................... G16H 50/70

FOREIGN PATENT DOCUMENTS

RU 2567037 C1 10/2015

OTHER PUBLICATIONS

Suchi Saria et al., "Integration of Early Physiological Responses Predicts Later Illness Severity in Preterm Infants", Science Translational Medicine, 2 (48), Sep. 8, 2010 (19 pages).
(Continued)

*Primary Examiner* — Garcia Ade
(74) *Attorney, Agent, or Firm* — HSML P.C.

(57) ABSTRACT

Disclosed herein is a method and a system for predicting risk of infection of a neonate. A neonate infection prediction system is configured to receive health data of the neonate from a wearable health monitoring device and a monitoring system, and evaluate baseline input data comprising a plurality of baseline physiological parameters of the neonate based on the health data. The system is configured to determine parameter values for baseline input data based on customized threshold data associated with each baseline physiological parameter, wherein the customized threshold data is determined using a customized threshold evaluation model. The system is further configured to evaluate a likelihood score based on the parameter values and predetermined weights and predict a risk of infection within the neonate based at least on the likelihood score.

20 Claims, 6 Drawing Sheets

(51) Int. Cl.
*A61B 5/0205* (2006.01)
*G16H 40/67* (2018.01)

(52) U.S. Cl.
CPC .......... *A61B 5/7275* (2013.01); *G16H 40/67* (2018.01); *A61B 2503/045* (2013.01)

(58) Field of Classification Search
CPC . A61B 5/7275; A61B 2503/045; A61B 5/412; G06Q 10/0635; G06Q 50/22
See application file for complete search history.

(56) References Cited

OTHER PUBLICATIONS

International Search Report and Written Opinion, International Patent Application No. PCT/IN/2022/050505, Sep. 22, 2022 (8 Pages).

Masino et al., "Machine learning models for early sepsis recognition in the neonatal intensive care unit using readily available electronic health record data", PLOS One, Feb. 22, 2019 (23 pages).

* cited by examiner

METHOD AND SYSTEM FOR RISK PREDICTION OF NEONATAL INFECTION

CROSS REFERENCE TO RELATED APPLICATION

This application claims the benefit of priority to Indian Provisional Patent Application Number 202141004156, filed on May 31, 2021, the entire contents of which are hereby incorporated by reference.

FIELD OF THE DISCLOSURE

Embodiments of the present disclosure are related, in general to risk analysis of infection in neonates, and more particularly, but not exclusively to a method and system for prediction of risk involved in neonatal infection.

BACKGROUND

Neonatal sepsis is a clinical syndrome characterized by signs and symptoms of infection that occurs in new-borns in first month of life. Neonatal sepsis encompasses various systemic infections of the new-born such as septicaemia, meningitis, pneumonia, arthritis, osteomyelitis, and urinary tract infections. Neonatal sepsis is a major cause of morbidity and mortality worldwide. Late onset neonatal sepsis (LONS) is responsible for most of the long-term morbidity and deaths in the Neonatal Intensive Care Unit (NICU). Sepsis causes a well-known series of physiologic changes including abnormalities of blood pressure, respiration, temperature, heart rate, and heart rate variability. Therefore, undetected and unmanaged symptoms of neonates can rapidly progress into severe sepsis and septic shock that is even more challenging to diagnose and doctors and caregivers do not get much time to act upon.

Though WHO recommends methods for clinically identifying early markers for sepsis, biomarker screening or empiric antibiotic therapy for every neonate with subtle nonspecific symptoms is the standard approach that is practiced by healthcare professionals. However, such strategies are unsatisfactory due to insufficient diagnostic accuracy of biomarkers and complications associated with overuse of antibiotics. Further, heart rate observation (HeRO) monitoring has been developed for detection of sepsis in preterm infants, wherein HeRO monitoring only analyses heart rate characteristics and displays clinicians a score that indicates risk of a neonate deteriorating from sepsis in next few hours. Such HeRO monitoring also requires high-end monitoring devices and costly resource settings. Consequently, challenges arise due to lack of systems and process to predict risk of sepsis and understand the level of risk to alert healthcare professionals in real time to avoid future health disorders in neonates.

Therefore, there is a need for a method and system to predict risk involved in neonatal sepsis or infection prior to obvious and catastrophic deterioration to the health of the neonate based upon the captured health parameters of the neonate in real time.

The information disclosed in this background of the disclosure section is only for enhancement of understanding of the general background of the disclosure and should not be taken as an acknowledgement or any form of suggestion that this information forms prior art already known to a person skilled in the art.

SUMMARY

Embodiments of the present disclosure relates to a method and system for prediction of infection risk in neonates. In one embodiment, a neonate infection prediction system is configured to receiving health data of the neonate from a wearable health monitoring device and a monitoring system, and evaluate baseline input data comprising a plurality of baseline physiological parameters of the neonate based on the health data. The system is configured to determine parameter values for baseline input data based on customized threshold data associated with each baseline physiological parameter, wherein the customized threshold data is determined using a customized threshold evaluation model. The system is further configured to evaluate a likelihood score based on the parameter values and predetermined weights and predict a risk of infection within the neonate based on one or more of the likelihood score and risk score. The system further generates an alert or notification upon determination of risk of infection to the neonate and transmits the generated alert or notification along with the risk score and information related to one or more health parameters to one or more monitoring systems.

The system provides an efficient and accurate prediction of infection in a neonate prior to any obvious and catastrophic changes in the neonate's health by using a wearable health monitoring device so as to enable healthcare professionals to take suitable action for mitigating health risk of the neonate.

BRIEF DESCRIPTION OF DRAWINGS

The accompanying drawings, which are incorporated in and constitute a part of this disclosure, illustrate exemplary embodiments and, together with the description, serve to explain the disclosed principles. In the figures, the left-most digit(s) of a reference number identifies the figure in which the reference number first appears. The same numbers are used throughout the figures to reference like features and components. Some embodiments of device or system and/or methods in accordance with embodiments of the present subject matter are now described, by way of example only, and with reference to the accompanying figures, in which.

Figure 1:
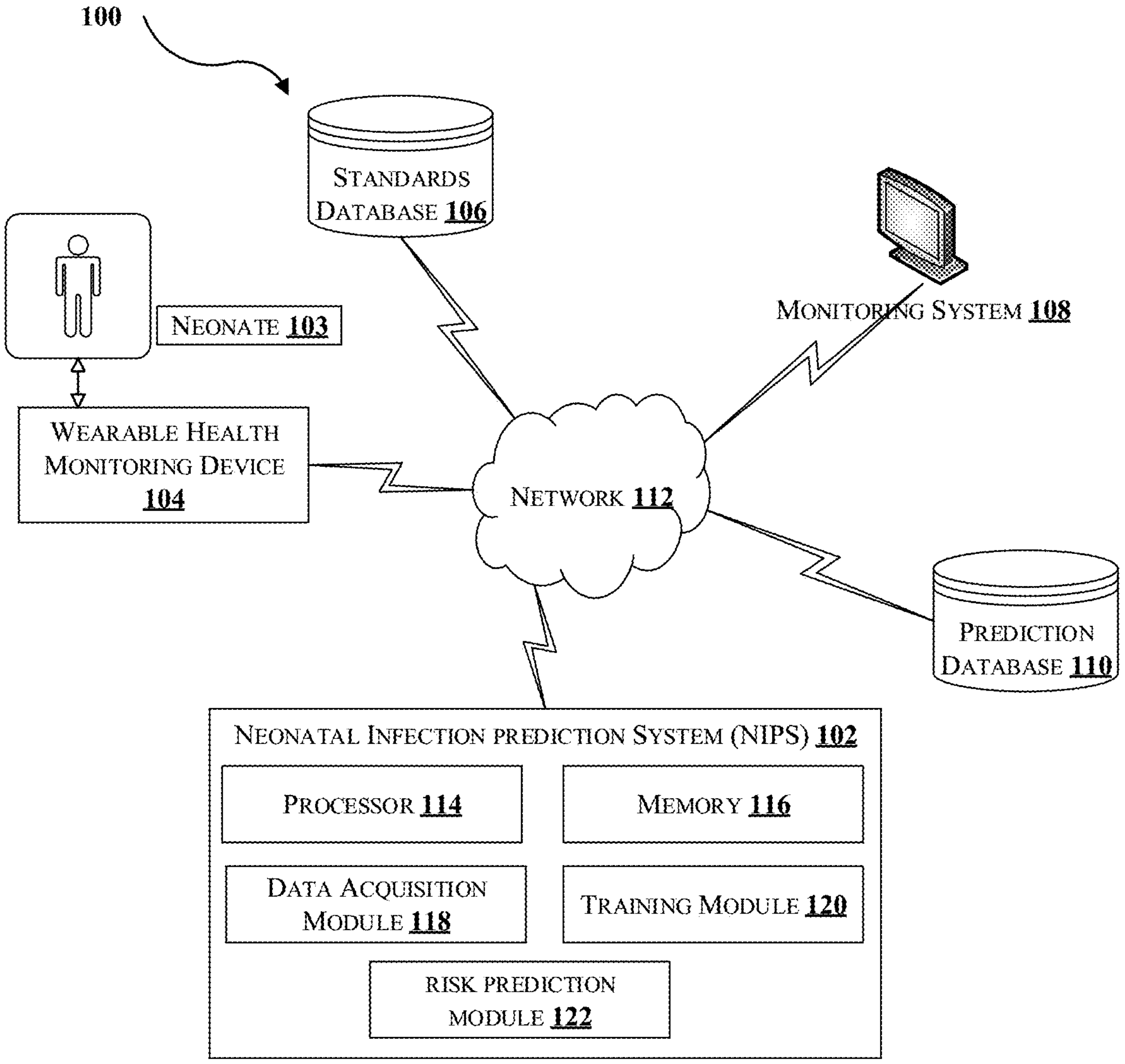
FIG. 1 illustrates an exemplary architecture of a proposed system to predict infection risk in neonates in accordance with some embodiments of the present disclosure.

The figures depict embodiments of the disclosure for purposes of illustration only. One skilled in the art will readily recognize from the following description that alternative embodiments of the structures and methods illustrated herein may be employed without departing from the principles of the disclosure described herein.

DETAILED DESCRIPTION

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiment thereof has been shown by way of example in the drawings and will be described in detail below. It should be understood, however that it is not intended to limit the disclosure to the particular forms disclosed, but on the contrary, the disclosure is to cover all modifications, equivalents, and alternative falling within the spirit and the scope of the disclosure.

The terms "comprises", "comprising", or any other variations thereof, are intended to cover a non-exclusive inclusion, such that a setup, device or method that comprises a list of components or steps does not include only those components or steps but may include other components or steps not expressly listed or inherent to such setup or device or method. In other words, one or more elements in a device or system or apparatus proceeded by "comprises . . . a" does not, without more constraints, preclude the existence of other elements or additional elements in the device or system or apparatus.

Embodiments of the present disclosure relates to a method and system for prediction of infection risk in neonates. In one embodiment, a neonate infection prediction system is configured to receiving health data of the neonate from a wearable health monitoring device and a monitoring system, and evaluate baseline input data comprising a plurality of baseline physiological parameters of the neonate based on the health data. The system is configured to determine parameter values for baseline input data based on customized threshold data associated with each baseline physiological parameter, wherein the customized threshold data is determined using a customized threshold evaluation model. The system is further configured to evaluate a likelihood score based on the parameter values and predetermined weights and predict a risk of infection within the neonate based on one or more of the likelihood score and risk score. The system further generates an alert or notification upon determination of risk of infection to the neonate and transmits the generated alert or notification along with the risk score and information related to one or more health parameters to one or more monitoring systems. The system provides an efficient and accurate prediction of infection in a neonate prior to any obvious and catastrophic changes in the neonate's health by using a wearable health monitoring device so as to enable healthcare professionals to take suitable action for mitigating health risk of the neonate.

In the following detailed description of the embodiments of the disclosure, reference is made to the accompanying drawings that form a part hereof, and in which are shown by way of illustration specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense.

FIG. 1 illustrates an exemplary architecture of a proposed system to predict of infection risk in neonates in accordance with some embodiments of the present disclosure.

As shown in FIG. 1, the exemplary system 100 comprises one or more components configured for predicting infection risk in neonates based upon medical requirements in real time. In one embodiment, the system 100 comprises a neonatal infection prediction system (NIPS) 102, at least one device such as a wearable health monitoring (WHM) device 104 associated with a subject such as neonate 103, a standards database 106, a monitoring system 108 and a prediction database 110 communicatively coupled via a communication network 112.

The communication network 112 may include, without limitation, a direct interconnection, LAN (local area network), WAN (wide area network), wireless network, point-to-point network, or another configuration. One of the most common types of network in current use is a TCP/IP (Transfer Control Protocol and Internet Protocol) network for communication between database client and database server. Other common Internet protocols used for such communication include HTTPS, FTP, AFS, and WAP and other secure communication protocols etc., for enabling communication with NIPS 102, the prediction database 110, the monitoring system 108 and the standards database 106.

The standards database 106 is capable of storing neonate data and medical reference data. The neonate data comprises plurality of health information of one or more neonates in the respective dataset received from one or more health monitoring systems, digital pathology systems, nursing stations etc. installed in health centres or hospitals. The plurality of health information includes but not limited to demographic data, maternal medical data, clinical data, laboratory data etc., of the neonates. The demographic data can include, but not limited to, gestational age, current age, birth weight, postnatal age, current weight, mode of delivery, number of apnoea events, indications/investigational data at birth etc. In an example, the maternal medical data can include, but not limited to, information related to neonate's mother such as antepartum, intrapartum, and postpartum data, accelerations and decelerations, contractions count, socio economic classification, maternal weight, age of mother, morbidity, marital status, educational level, occupational status, parity, mode of delivery, number of antenatal visits, hypertensive disorders, bleeding disorder, and Premature rupture of membrane (PROM), maternal history of urinary tract infection (UTI)/STI, prolonged labour, presence or absence of Cervicovaginitis and chorioamnionitis.

In one example, the clinical data can include, but not limited to, information related to blood pressure. Glasgow coma scale score, carbon dioxide pressure, serum bicarbonate levels, tidal volume, airway pressure, urine output, hypothermia (Hypo), tachycardia (TC), bradycardia (BC), tachypnoea (TA), bradypnea (BA) etc and heart rate variability, pleth variability index, core periphery temperature gradient, saturation variability, temperature gradient variability, perfusion index variability, and respiration rate variability. In another example, the laboratory data can include, but not limited to, information related to biochemical analysis such as bilirubin, urine, white blood cell count, red blood cell count, platelet count, bilirubin level, albumin level. pH, potassium level, sodium level, creatinine level, blood urea nitrogen, glucose level, haemoglobin, immature to total neutrophil (I/T) ratio, capillary pH etc. The standards database 106 also stores medical reference data 214 comprising, past analysis of neonatal infection by medical practitioners, healthcare workers, medical prescriptions associated with neonatal infection, and one or more parameters considered to predict neonatal infection. The standards database 106 also stores the demographic data and the maternal medical data measured for a plurality of neonates and their corresponding standard values for each baseline physiological parameter. In one example, the standards database 106 may be integrated within the NIPS 102. The standards database 106 may be configured, for example, as a standalone data store or as a cloud data storage as illustrated and communicatively coupled with the one or more health care monitoring systems, digital pathology systems, nursing stations etc. to receive the plurality of health information of the neonates.

The prediction database 110 is capable of storing low resolution data 208 comprising demographic data, maternal medical data and laboratory data as described above of a plurality of neonates measured in the past. The low resolution data 208 is measured at a rate of one sample or more per hour. The prediction database 110 may also store information related to high resolution data, which is the clinical data of the neonate measured at high resolutions of at least one sample or more per second Further, the prediction database may also store information related to baseline data 212, derived from the high resolution data 210, comprising heart rate variability, pleth variability index, core periphery temperature gradient, saturation variability, temperature gradient variability, perfusion index variability, and respiration rate variability. The baseline data 212 comprises both the baseline training data and baseline input data of a plurality of neonates measured in the past and used to predict the risk of infection.

The prediction database 110 is capable of storing historical data including plurality of operational data of prediction of infection risk of neonates in the respective dataset. The prediction database 110 is configured to store training data comprising a plurality of past values of low resolution data, high resolution data, likelihood scores of neonatal infection for a plurality of neonates, a plurality of values and weights associated with a plurality of baseline physiological parameters corresponding to each of the plurality of likelihood scores, and plurality of predicted values of risk of infection. The prediction database 110 is configured to store training data comprising plurality of information such as historical prediction information, plurality of parameters to be used in prediction process, a plurality of significant parameters, a plurality of neonatal profiles, optimized weightages of such significant parameters, risk scores associated with infection prediction, a plurality of risk prediction models used to determine the risk scores, etc. The prediction database 110 is also configured to store training datasets comprising past history of local threshold data, global threshold data and customized threshold data for each baseline physiological parameter for a plurality of neonates. In one example, the prediction database 110 may be integrated within the NIPS 102. The prediction database 110 may be configured, for example, as a standalone data store or as a cloud data storage as illustrated.

The WHM device 104 may be a wearable health monitoring device or a wearable computing device associated with the neonate to capture one or more health parameters of the neonate by non-invasive monitoring of blood analytes. The WHM device 104 captures the high resolution data i.e., one or more health parameters corresponding to the clinical data at high resolution speed, for example one sample or more per second. The WHM device 104 can comprise one or more photodetectors, one or more thermistors, a motion detection sensor, one or more electrodes, one or more microfluidic channels in order to capture high resolution data.

The WHM device 104 also includes the functionality for communicating over the communication network 112. In one embodiment, the WHM device 104 is configured with a microprocessor that enables interaction with the NIPS 102 for communicating captured health information to the NIPS 102. For example, the microprocessor in the WHM device 104 is configured to transmit one or more captured health information such as heart rate, body temperature, oxygenation levels, body position, respiration rate, ECG data, glucose levels heart rate variability, etc., to the NIPS 102 in real time. In one embodiment, the health information captured by the WHM device 104 is stored in the prediction database 110 for risk prediction process.

The monitoring system 108 may be any electronic output device capable of presenting information related to health information of the neonate, wherein such output device can be one of plurality of available display devices such as CRT (Cathode Ray Tube) display. LED (Light-emitting diode) display. LCD (Liquid Crystal Display). QLED (Quantum dot Display) etc. One or more display units can be installed in suitable locations such as NICUs (Neonatal Intensive Care Unit) of hospital, health monitoring stations etc. so that one or more healthcare professionals can access health information of one or more neonates in continuous manner and receive alerts in case of emergency. In one embodiment, the monitoring system 108 can be configured with a touch-based user interface so that the healthcare professionals such as neonatologists, nurses etc. can operate on the monitoring system 108 for enquiring display of plurality of neonatal health information and prediction infection information as determined by the NIPS 102.

In one embodiment, the monitoring system 108 may also include electronic input devices such as a mouse, touch pad, keyboard, or stylus-enabled devices to enable healthcare professionals such as neonatologists, nurses etc to input data related to the neonate into the NIPS 102. For example, the monitoring system may receive information about the neonate such as the demographic data that can include gestational age, current age, birth weight, postnatal age, current weight, mode of delivery, number of apnoea events, indications/investigational data at birth etc. The NIPS 102 may be configured as a cloud-based implementation server or as a standalone server. In one embodiment, the NIPS 102 comprises a processor 114 and a memory 116 coupled to the processor 114 that stores processor-executable instructions. In one embodiment, the NIPS 102 includes a plurality of data that are stored within the memory 116. In one example, the plurality of data may include captured health parameter data, historical medical record of neonates, clinical evaluation information, risk data and other data. In one embodiment, the plurality of data can be stored in the memory 116 in the form of various data structures. Additionally, the aforementioned data can be organized using data models, such as relational or hierarchical data models. The memory 116 may also store data, including temporary data, temporary files, health parameter processing data, machine learning data for performing the various functions of the NIPS 102.

The NIPS 102 further comprises one or more modules configured to predict infection risk in neonates based upon medical requirements in real time. In one embodiment, the one or more modules include a data acquisition module 118, a training module 120, a risk prediction module 122 and other modules 124. The NIPS 102 is configured to facilitate healthcare professionals to continuously monitor, predict health risk status including information related to plurality of critical health parameters of one or more neonates under supervision. The NIPS 102 further facilitates the healthcare professionals by providing early warning scores based on analyses of health parameters with respect to clinical evaluation parameters such as thresholds, normalcy ranges etc., that are used by the healthcare professionals to prognose early/late onset of infection, for example, sepsis, in neonates. Therefore, the NIPS 102 provides an efficient system that accurately predict infection risk in a neonate prior hand so as to enable healthcare professionals to take suitable action for mitigating infection risk of the neonate.

Figure 2:
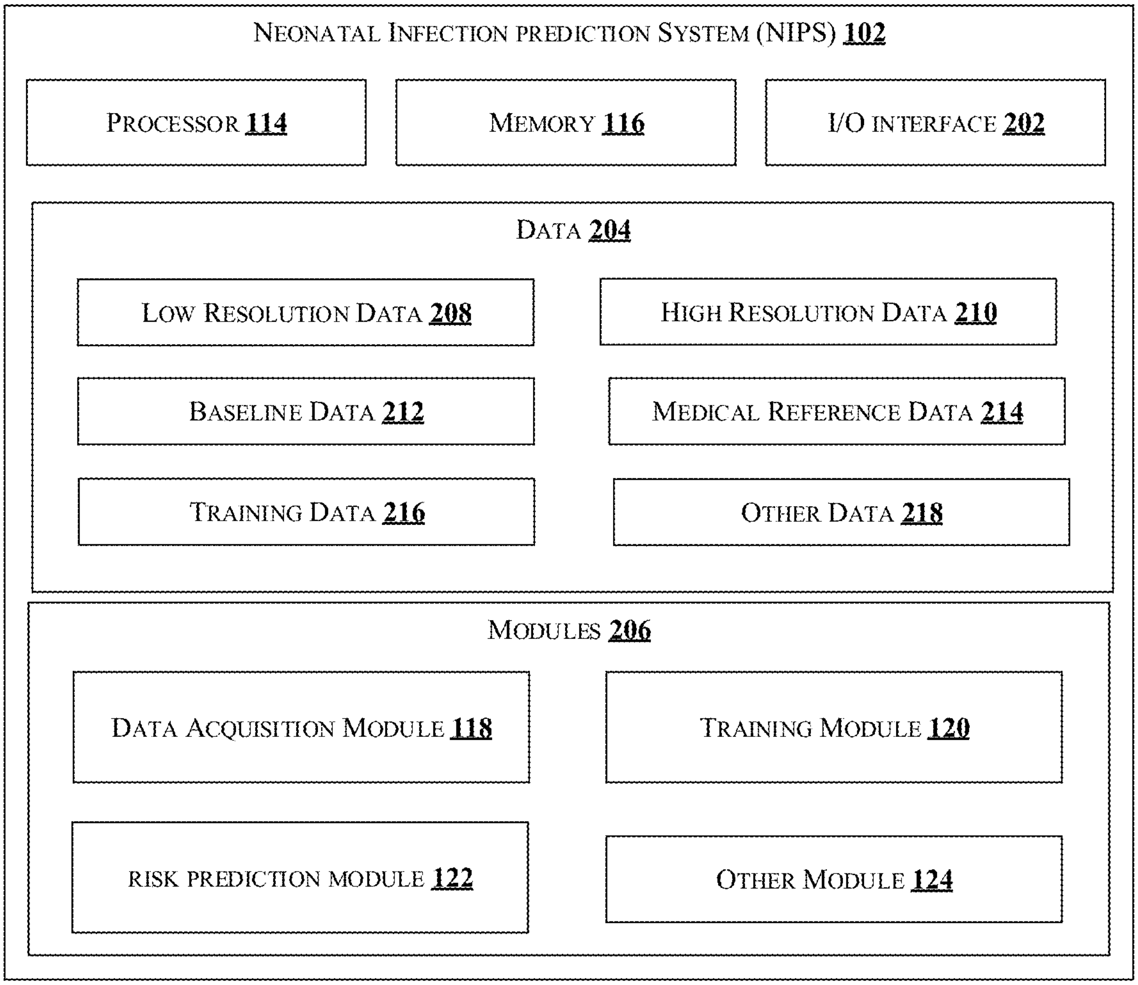
FIG. 2 illustrates an exemplary block diagram of a neonatal infection prediction system (NIPS) of the FIG. 1 in accordance with some embodiments of the present disclosure.

In an embodiment, the NIPS 102 may be a typical NIPS as illustrated in FIG. 2. The NIPS 102 comprises the processor 114, the memory 116, and an I/O interface 202. The I/O interface 202 is coupled with the processor 114 and an I/O device (not shown). The I/O device is configured to enable the processor 114 to communicate with and control from various I/O devices. The I/O device is configured to receive input via the I/O interface 202 and transmit output via the I/O interface 202. The NIPS 102 further includes data 204 and one or more modules 206. In one implementation, data 204 may be stored within the memory 116. In one example, the data 204 may include low resolution data 208, high resolution data 210, baseline data 212, medical reference data 214, training data 216 and other data 218. In some embodiments, the data 204 may be stored within the memory 116 in the form of various data structures. Additionally, the data 204 may be organized using data models, such as relational or hierarchical data models. The other data 218 may store temporary data and temporary files, generated by the components for performing the various functions of the NIPS 102.

In one embodiment, the data acquisition module 118 receives high resolution data 210 of the neonate as captured by the WHM device 104 in real time from the time of birth, derives baseline training data from the high resolution data and stores the baseline training data, in the prediction database 110. The data acquisition module 118 receives plurality of other health information such as low threshold data 208 comprising demographic data, maternal medical data, laboratory data etc. of the neonate from the monitoring system stored in the standards database 106. In one embodiment, the data acquisition module 118 may receive the laboratory data directly from one or more computing systems of pathology centres over the communication network 112.

The data acquisition module 118 further temporarily stores the plurality of other health information of the neonate in the prediction database 110 for enabling early prediction of infection risk. The plurality of baseline physiological parameters include, but not limited to, heart rate variability, pleth variability index, core periphery temperature gradient, saturation variability, temperature gradient variability, perfusion index variability, and respiration rate variability that are derived from captured high resolution data 210.

Further, the data acquisition module 118 stores a plurality of training datasets in the prediction database 110 for training two machine learning models used to predict infection risk within the neonate, wherein the plurality of training datasets is received from one or more external sources. The two machine learning models comprise a first machine learning model, also referred herein as a likelihood prediction model, to evaluate a likelihood score of the infection in the neonate 103 and a second machine learning model, also referred herein as a risk prediction model, to evaluate a risk score of the infection in the neonate 103. The first machine learning model further comprises a customized threshold evaluation model which is another machine learning model to evaluate customized threshold data for the neonate 103. The plurality of training datasets include historical information related to symptoms, vital health parameters, and other neonatal health parameters of healthy neonates and neonates suffered from infection. The data acquisition module 118 stores one or more pre-defined threshold values as defined by standard medical guidelines in the prediction database 110, wherein the one or more pre-defined threshold values may include medically defined standard ranges of different health parameters of neonates. In another embodiment, the data acquisition module 118 is configured to accumulate the historical information related to vital health parameter and other neonatal health parameters for one or more neonates over a period of time and store the accumulated information in the prediction database 110.

The data acquisition module 118 stores training datasets associated with likelihood prediction model comprising a plurality of past values of low resolution data, high resolution data, for a plurality of neonates. The data acquisition module 118 stores training datasets associated with the likelihood prediction model further comprising a plurality of values of likelihood scores of neonatal infection for a plurality of neonates, a plurality of values and weights associated with a plurality of baseline physiological parameters corresponding to each of the plurality of likelihood scores, and plurality of predicted values of risk of infection. The data acquisition module 118 also stores other training datasets associated with customized threshold evaluation model comprising a plurality of past values of local threshold data, global threshold data and customized threshold data for each baseline physiological parameter of the neonate 103. The data acquisition module 118 stores other training datasets associated with risk prediction model comprising plurality of information such as historical prediction information, plurality of parameters to be used in prediction process, a plurality of significant parameters, a plurality of neonatal profiles, optimized weightages of such significant parameters, risk scores associated with infection prediction, a plurality of risk prediction models used to determine the risk scores, etc.

Each machine learning model is a representation of complex computational technique of prediction of infection risk. The complex computational technique can include but not limited to relevant machine learning algorithms such as approaches based on clustering, neural networks etc. In one embodiment, each machine learning model is trained to recognize a certain type of patterns by using the training datasets as stored in the prediction database 110 by the data acquisition module 118.

The training module 120 retrieves the training datasets from the prediction database 110 and performs training of machine learning models associated with the two machine learning models by feeding the training datasets to each machine learning model. The plurality of machine learning models may include, but not limited to, Logistic Regression algorithm, Gaussian Process algorithm, K-nearest neighbor (KNN) algorithm, support vector machine (SVM) algorithm, Random Forest algorithm, AdaBoost algorithm, Gradient Boosting algorithm, Gaussian Process algorithm, weighted average model and Gaussian Naive Bayes algorithm.

The training module 120 retrieves training datasets associated with the customized threshold evaluation model and determines the customized threshold data particular for the neonate 103, which is later used as training dataset to evaluate the likelihood score for the neonate 103. The determination of the customized threshold data is explained herein with reference to FIG. 3.

Figure 3:
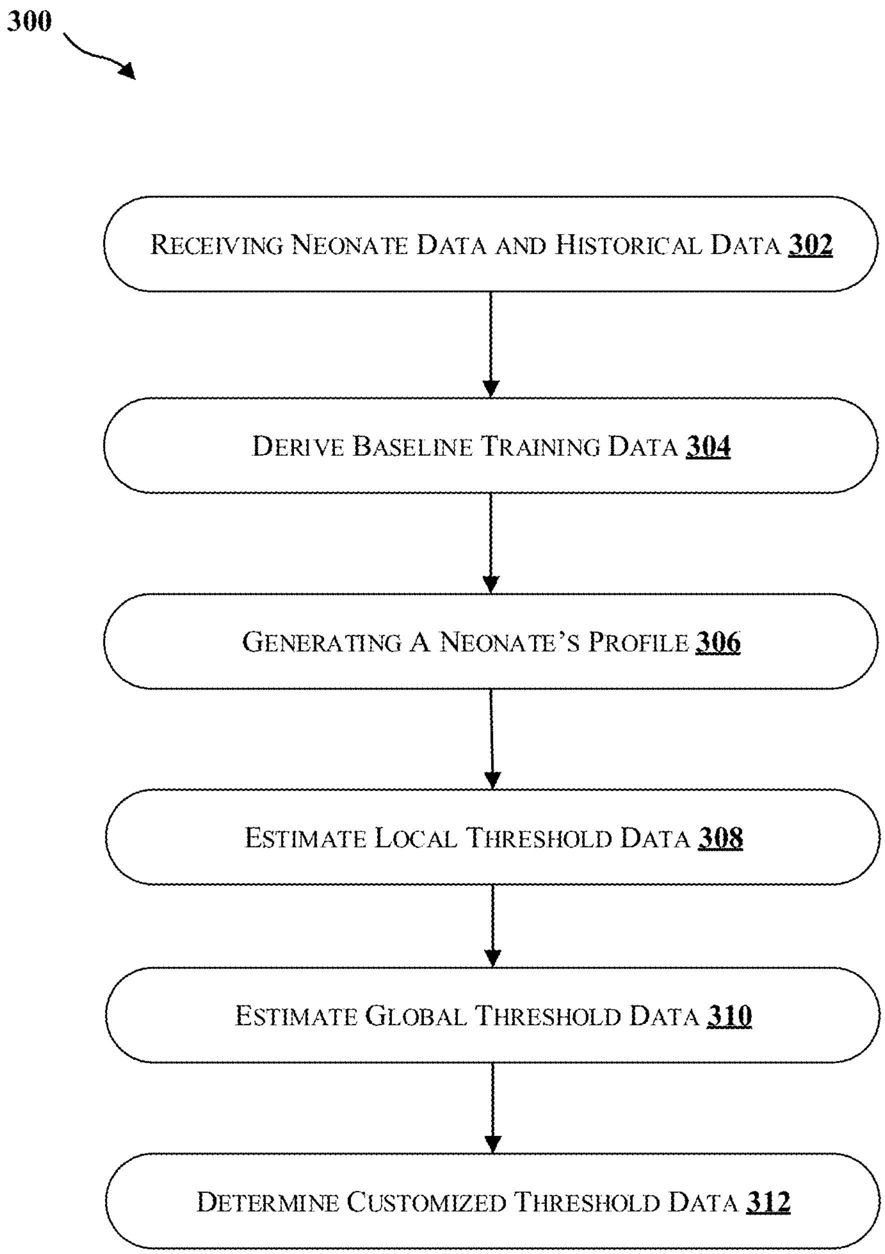
FIG. 3 illustrates a flowchart showing a method for determining the customized threshold data in accordance with some embodiments of the present disclosure.

FIG. 3 illustrates a flowchart showing a method for determining the customized threshold data in accordance with some embodiments of the present disclosure;

As illustrated in FIG. 3, the method 300 comprises one or more blocks implemented by the processor 114 to determine customized threshold data particular for the neonate by using NIPS 102. The method 300 may be described in the general context of computer executable instructions. Generally, computer executable instructions can include routines, programs, objects, components, data structures, procedures, modules, and functions, which perform specific functions or implement specific abstract data types.

The order in which the method 300 is described is not intended to be construed as a limitation, and any number of the described method blocks can be combined in any order to implement the method. Additionally, individual blocks may be deleted from the methods without departing from the spirit and scope of the subject matter described herein. Furthermore, the method can be implemented in any suitable hardware, software, firmware, or combination thereof.

At block 302, the training module 120 receives neonate data of the neonate 103 and historical data. The training module 120 receives the neonate data of the neonate 103 that comprises past values of low resolution data including demographic data, maternal medical data, laboratory data and high resolution data associated with the neonate 103, preferably when the health status of the neonate 103 is normal i.e., without any infection. In one example, the neonate 103 is assumed not to have any infection at the time of birth and that the health status of neonate 103 is normal at the time of birth. In another example, the neonate data is collected during the first one hour from the time at which the neonate 103 is born. In another example, the neonate data is collected during the first ten minutes from the time at which the neonate 103 is born. The training module 120 also receives the historical data that comprises the training data 216 from the prediction database 110 and the medical reference data 214 from the standards database 106. The training module 120 further receives the low resolution data 208 at a low resolution, such as at a rate equal to or greater than one sample per hour and the high resolution data 210 at a high resolution such as at a rate equal to or more than one sample per second.

At block 304, the training module 120 derives baseline training data comprising values of baseline physiological parameters based on the high resolution data 210, when the neonate 103 is normal and stores the baseline training data in the baseline data 212. The training module 120 evaluates at least one of time varying and frequency varying trends of the baseline physiological parameters. The baseline physiological parameters include, but not limited to, heart rate variability, pleth variability index, core periphery temperature gradient, saturation variability, temperature gradient variability, perfusion index variability, and respiration rate variability. The training module 120 evaluates the trends based on the high resolution data captured from the WHM device 104 worn by the neonate 103.

At block 306, the training module 120 generates a neonate profile based on the evaluated trends of the baseline physiological parameters. The neonate profile indicates the health behaviour of the neonate 103 during normal health conditions. For example, the neonate profile of the neonate 103 indicates a range of a normal value of each baseline physiological parameter of the neonate 103 during the neonate's normal health status.

At block 308, the training module 120 estimates local threshold data for the baseline training data based on the neonate profile which indicates the normal health status of the neonate 103. The local threshold data comprises a plurality of local threshold values each associated with each one of a plurality of baseline physiological parameters of the neonate 103. The local threshold value indicates the threshold value of each baseline physiological parameter only based on the data measured from the neonate 103.

At block 310, the training module 120 estimates global threshold data for the baseline training data based on the neonate's demographic data and the maternal medical data by referring to the medical reference data 214. The global threshold data comprises a plurality of global threshold values associated with each of the plurality of baseline physiological parameters. A global threshold value indicates a medical threshold value of the baseline physiological parameter determined based on the neonate's demographic data and the maternal medical data by referring to the medical reference data 214. For example, the training module 120 compares the demographic data and the maternal medical data measured for the neonate 103 with any of the existing demographic data and the maternal medical data within the standards database 106 and retrieves a standard value for the baseline physiological parameter that is associated with the demographic data and the maternal medical data. The retrieved standard value is the medical threshold value for the baseline physiological parameter.

At block 312, the training module 120 determines the customized threshold data particularly for the neonate 103. The training module 120 provides the local threshold data and the global threshold data associated with baseline training data to a trained customized threshold evaluation model, which outputs the customized threshold data for baseline training data. The customized threshold evaluation model may be a machine learning model among at least one of regression model, curve fitting model, support vector machine model or any other known machine learning model used to determine the customized threshold data for each baseline training data. The training module 120 trains the customized threshold evaluation model using a training dataset comprising past history of baseline training data, demographic data, maternal medical data, a plurality of medical threshold values associated with each set of the values, past history of local threshold data, global threshold data and their corresponding customized threshold data, retrieved from the prediction database 110 and the standards database 106.

The training module 120 retrieves training datasets related to the likelihood prediction model and defines a weight associated with each of the baseline physiological parameters based on the analysis of the medical reference data 214. In one embodiment, the training module 120 can dynamically update weightage for each of the baseline physiological parameters based on health data of the neonate 103 received in real time. The training module 120 also retrieves training datasets associated with the risk prediction model comprising a plurality of neonatal profiles generated earlier by the risk prediction module 122 and stored in the prediction database 110. The training module 120 further retrieves a risk prediction model that performs better for the neonatal profile of the neonate for which infection is to be predicted. The risk prediction model may be any one of Logistic Regression algorithm, Gaussian Process algorithm, K-nearest neighbor (KNN) algorithm, support vector machine (SVM) algorithm, Random Forest algorithm, AdaBoost algorithm, Gradient Boosting algorithm, Gaussian Process algorithm, and Gaussian Naive Bayes algorithm. The training module 120 trains the risk prediction model used to evaluate a risk score of the neonate 103.

The training module 120 uses the training datasets to train each machine learning model such as the customized threshold evaluation model, likelihood prediction model and the risk prediction model. The training module 120 processes the training datasets in one or more phases to prepare a training data and a testing data, wherein the one or more phases include but not limited to analysis of data, handling missing data, cleansing of data, deciding key factors related to data etc. The training module 120 further splits the training data into a plurality of mini batches so that the process of training can be conducted in a plurality of iterations. Once the machine learning model receives each of the mini-batches as input, the machine learning model initiates the learning from the information contained in each of the mini-batches, wherein the machine learning model can use one of plurality of learning mechanism such as supervised learning, unsupervised learning etc. The training of the machine learning model is completed upon processing all the mini batches. Further, the training module 120 performs testing of the trained machine learning model using the testing data to ensure desired performance of the machine learning model. The trained machine learning model further receives captured vital health parameters from the WHM device 104 and additional medical information for the neonate for predicting infection risk in the neonate prior to any kind of deterioration to health of the neonate. In one embodiment, upon completion of the initial training process, the machine learning model continuously learns from the processing of one or more received neonatal information in real time.

The risk prediction module 122 receives information acquired by the data acquisition module 118 to predict risk of infection in a neonate. The prediction of risk of infection in a neonate performed by the risk prediction module 122 is hereby explained in view of FIGS. 4 and 5.

Figure 4:
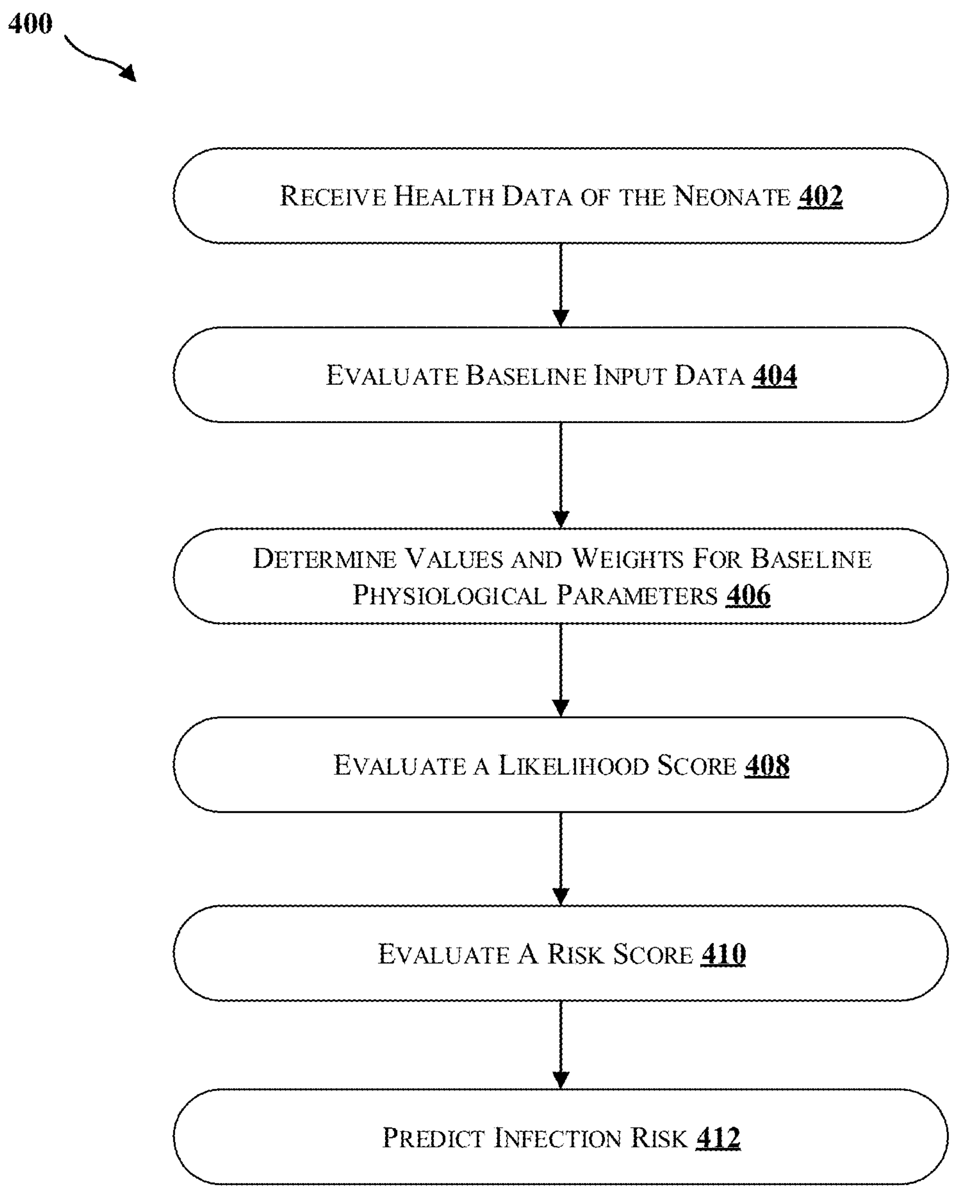
FIG. 4 illustrates a flowchart showing a method for predicting infection risk in neonates in accordance with some embodiments of the present disclosure.
Figure 5:
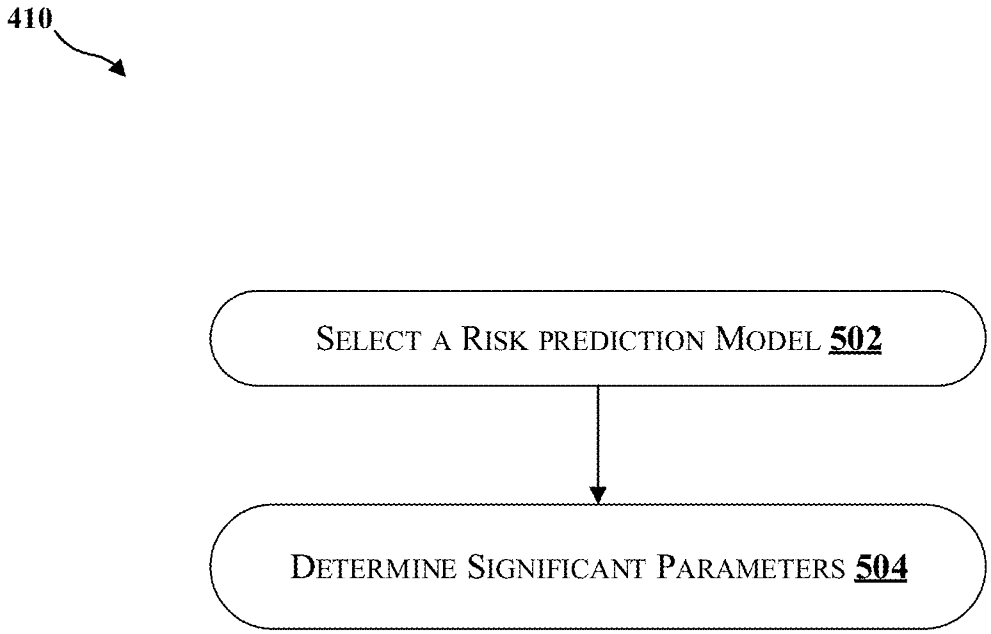
FIG. 5 illustrates a flowchart showing a method for evaluating a risk score of the FIG. 4 in accordance with some embodiments of the present disclosure.

FIG. 4 illustrates a flowchart showing a method for predicting infection risk in neonates in accordance with some embodiments of the present disclosure.

As illustrated in FIG. 4, the method 400 comprises one or more blocks implemented by the processor 114 to predict risk of infection in the neonate using two machine learning models by using NIPS 102. The method 400 may be described in the general context of computer executable instructions. Generally, computer executable instructions can include routines, programs, objects, components, data structures, procedures, modules, and functions, which perform specific functions or implement specific abstract data types.

The order in which the method 300 is described is not intended to be construed as a limitation, and any number of the described method blocks can be combined in any order to implement the method. Additionally, individual blocks may be deleted from the methods without departing from the spirit and scope of the subject matter described herein. Furthermore, the method can be implemented in any suitable hardware, software, firmware, or combination thereof.

At block 402, the risk prediction module 122 receives health data of the neonate 103. The health data of the neonate 103 comprises current values of low resolution data including demographic data, maternal medical data, laboratory data and high resolution data of the neonate 103 measured at a current period of time. The risk prediction module 122 receives the low resolution data 208 at a low resolution, such as at a rate equal to or greater than one sample per hour and the high resolution data 210 at a high resolution such as at a rate equal to or more than one sample per second. The risk prediction module 122 collects the high resolution data 210 from the time at which the neonate 103 is born from the WHM device 104. The current period of time can vary from a few seconds to a few hours at the current time. For example, the current period of time corresponds to data measured during last minute or last hour.

At block 404, the risk prediction module 122 evaluates baseline input data comprising the current values of baseline physiological parameters based on the received current data. The risk prediction module 122 receives the high resolution data of the neonate 103 from the WHM device 104 and evaluates the current values of the baseline physiological parameters including heart rate variability, pleth variability index, core periphery temperature gradient, saturation variability, temperature gradient variability, perfusion index variability, and respiration rate variability.

At block 406, the risk prediction module 122 determines parameter values of each baseline physiological parameter based on the baseline input data and the customized threshold data, determined by the training module 120 as described in the above paragraphs. The risk prediction module 122 compares baseline input data of a baseline physiological parameter with customized threshold data associated with the baseline parameter. For example, the risk prediction module 122 compares the current value of a baseline parameter such as heart rate variability with the customized threshold value of the heart rate variability determined by the training module 120. The risk prediction module 122 further determines a first value, for e.g., "1", to the baseline physiological parameter if baseline input data comprising the current value of the baseline physiological parameter exceeds the customized threshold data comprising determined customized threshold value associated with the baseline parameter. The risk prediction module 122 determines a second value, for e.g., "2", to the baseline physiological parameter if the baseline input data comprising current value of the baseline physiological parameter is lesser than or equal to the customized threshold data comprising determined customized threshold value associated with the baseline physiological parameter.

At block 408, the risk prediction module 122 evaluates the likelihood score based on the determined values to each baseline physiological parameter and retrieved predetermined weights for each baseline physiological parameter. The risk prediction module 122 retrieves predetermined weights for each baseline physiological parameter based on the medical reference data 214. The predetermined weights are stored in the standards database 106 and are determined based on the past analysis of neonatal infection by medical practitioners, healthcare workers, medical prescriptions associated with neonate infection, and one or more parameters considered to predict neonatal infection, and priority associated with each parameter to predict neonatal infection. In some embodiments, the likelihood score can alone be used to predict the risk of infection, compared to a threshold for the likelihood score. For example, if the likelihood score exceeds a threshold of 70%, the neonate 103 is more likely to have an infection such as late onset sepsis. In another example, if the likelihood score is less than the threshold of 70%, the neonate 103 is less likely to have the infection. The greater is the difference between the likelihood score and the threshold, the more likely or the less likely is the neonate 103 to have the infection. In some other embodiments, the likelihood score in combination with risk score is used to predict the risk of infection within the neonate 103.

At block 410, the risk prediction module 122 evaluates a risk score that indicates a risk of the neonate 103 having infection. The method of evaluating the risk score is further explained in detail during the explanation of FIG. 5.

At block 502, the risk prediction module 122 selects an risk prediction model based on the neonate profile and training data from the prediction database 110. The training data comprises historical data of a plurality of risk prediction models associated with a plurality of neonate profiles, and a plurality of significant parameters associated with a plurality of neonate profiles. For example, the training data may comprise a one to many or many to one or many to many relationship between the plurality of neonate profiles, a plurality of significant parameters and the plurality of risk prediction models. The training data may also be stored in wide variety of other known forms such as, but not limited to, graphical data structure, tabular form. The risk prediction module 122 compares the neonate profile of the neonate 103 with a plurality of neonate profiles within the training data and detects a neonate profile that is similar to the neonate profile of the neonate 103. The risk prediction module 122 retrieves a risk prediction model that is associated with the identified neonate profile. The risk prediction module 122 compares the similarity between the neonate profile of the neonate 103 and the plurality of neonate profiles within the training data based on any known method such as evaluating differences, variances, similarity scores associated with each parameter of the neonate profile and plurality of neonate profiles within the training data. The risk prediction model can be a machine learning model including, but not limited to. Logistic Regression algorithm, Gaussian Process algorithm, K-nearest neighbor (KNN) algorithm, support vector machine (SVM) algorithm, Random Forest algorithm, AdaBoost algorithm, Gradient Boosting algorithm, Gaussian Process algorithm, and Gaussian Naive Bayes algorithm. The risk prediction module 122 may retrieve a trained model of the selected risk prediction model trained by the training module 120.

At block 504, the risk prediction module 122 determines significant parameters based on the training data and the neonate profile of the neonate 103. Significant parameters indicate a set of parameters that are significant for use by the risk prediction model associated with the neonate profile to predict the risk of infection within the neonate 103. Significant parameters may include hyper parameters that are provided as input to the risk prediction model to determine the risk score. The risk prediction module 122 determines the significant parameters by retrieving a set of significant parameters associated with the identified neonate profile stored in the training data 216. The significant parameters may include any combination of health parameters including, but not limited to, the low resolution data 208, the high resolution data 210, and the baseline data 212 of the neonate 103.

Referring to FIG. 4, at block 410, the risk prediction module 122 evaluates the risk score based on the significant parameters and the risk prediction model. The risk prediction module 122 provides the values of the significant parameters that are received as the health data of the neonate 103 at current period of time to the trained risk prediction model at block 502. The trained risk prediction model evaluates the risk score based on the significant parameters chosen for the neonate 103. The risk prediction model may generate any of three values for the risk score which indicates the probability of infection in the neonate 103. The risk prediction model may generate a value of "+1" which indicates that the neonate is more likely to have infection, a value of "0" which indicates that the risk needs to be evaluated again, and a value of "−1" which indicates that the neonate 103 is very less likely to have the infection.

At block 412, the risk prediction module 122 predicts the infection risk within the neonate 103 by combining the likelihood score and the risk score. For example, the risk prediction module 122 predicts that the neonate is highly likely to have an infection if the likelihood score is greater than 70% and the risk score is "+1". In another example, the risk prediction module 122 predicts that the neonate is very less likely to have an infection if the likelihood score is 30% and the risk score is "−1".

In some embodiments, the risk prediction module 122 generates alert that contains details of the associated risk in one or more formats suitable for one or more transmission modes such as SMS (Short Message Services), email, app notification, automated phone calls etc. The risk prediction module 122 transmits the generated alert or notification along with the risk score and information related to one or more health parameters responsible for probable infection to the monitoring system 108 or respective personal devices of one or more healthcare professionals authorized for supervise the neonate. The risk prediction module 122 further generates one or more actions items recommended for respective infection risk, wherein the actions items include providing suitable antibiotic exposure, performing recommended pathological tests etc.

The NIPS 102 is configured to facilitate healthcare professionals to continuously monitor, predict health risk status including information related to plurality of critical health parameters of one or more neonates under supervision. The NIPS 102 further facilitates the healthcare professionals by providing early warning scores based on analyses of health parameters with respect to clinical evaluation parameters such as thresholds, normalcy ranges etc., that are used by the healthcare professionals to prognose early/late onset of infection, for example, sepsis, in neonates. Therefore, the NIPS 102 provides an efficient system that accurately predict infection risk in a neonate prior hand so as to enable healthcare professionals to take suitable action for mitigating infection risk of the neonate.

Figure 6:
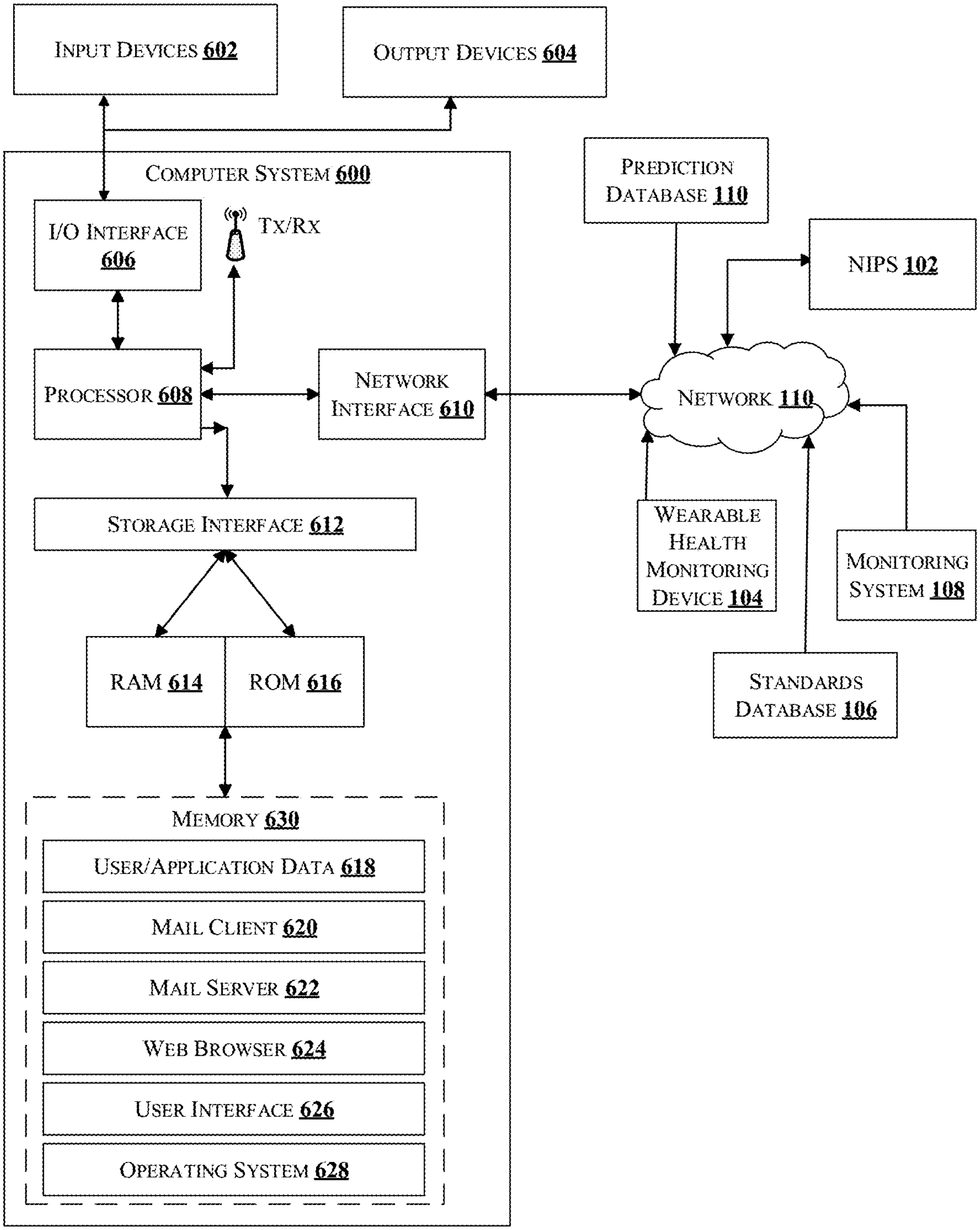
FIG. 6 illustrates a block diagram of an exemplary computer system for implementing embodiments consistent with the present disclosure.

FIG. 6 illustrates a block diagram of an exemplary computer system for implementing embodiments consistent with the present disclosure.

In an embodiment, the computer system (600) may be neonatal infection prediction system 102, which is used for receiving vital health parameters' information from neonates and predicting probability of neonatal infection early in real time. The computer system (600) may include a central processing unit ("CPU" or "processor") (608). The processor (608) may comprise at least one data processor for executing program components for executing user or system-generated business processes. The processor (608) may include specialized processing units such as integrated system (bus) controllers, memory management control units, floating point units, graphics processing units, digital signal processing units, etc.

The processor (608) may be disposed in communication with one or more input/output (I/O) devices (602 and 604) via I/O interface (606). The I/O interface (606) may employ communication protocols/methods such as, without limitation, audio, analog, digital, stereo, IEEE-1694, serial bus, Universal Serial Bus (USB), infrared, PS/2, BNC, coaxial, component, composite, Digital Visual Interface (DVI), high-definition multimedia interface (HDMI), Radio Frequency (RF) antennas, S-Video, Video Graphics Array (VGA), IEEE 802.n/b/g/n/x, Bluetooth, cellular (e.g., Code-Division Multiple Access (CDMA), High-Speed Packet Access (HSPA+), Global System For Mobile Communications (GSM), Long-Term Evolution (LTE) or the like), etc.

Using the I/O interface (606), the computer system (600) may communicate with one or more I/O devices (602 and 604). In some implementations, the processor (608) may be disposed in communication with a communication network 112 via a network interface (610). The network interface (610) may employ connection protocols including, without limitation, direct connect, Ethernet (e.g., twisted pair 10/100/1000 Base T), Transmission Control Protocol/Internet Protocol (TCP/IP), token ring, IEEE 802.11a/b/g/n/x, etc. Using the network interface (610) and the communication network 112, the computer system (600) may be connected to the NIPS 102, the WHM device 104, the standards database 106, the monitoring system 108, and the prediction database 110.

The communication network 112 can be implemented as one of the several types of networks, such as intranet or any such wireless network interfaces. The communication network 112 may either be a dedicated network or a shared network, which represents an association of several types of networks that use a variety of protocols, for example, Hypertext Transfer Protocol (HTTP), Transmission Control Protocol/Internet Protocol (TCP/IP), Wireless Application Protocol (WAP), etc., to communicate with each other. Further, the communication network 112 may include a variety of network devices, including routers, bridges, servers, computing devices, storage devices, etc.

In some embodiments, the processor (608) may be disposed in communication with a memory (660) e.g., RAM (614), and ROM (616), etc. as shown in FIG. 6, via a storage interface (612). The storage interface (612) may connect to memory (660) including, without limitation, memory drives, removable disc drives, etc., employing connection protocols such as Serial Advanced Technology Attachment (SATA), Integrated Drive Electronics (IDE), IEEE-1694, Universal Serial Bus (USB), fiber channel, Small Computer Systems Interface (SCSI), etc. The memory drives may further include a drum, magnetic disc drive, magneto-optical drive, optical drive, Redundant Array of Independent Discs (RAID), solid-state memory devices, solid-state drives, etc.

The memory (660) may store a collection of program or database components, including, without limitation, user/application (618), an operating system (628), a web browser (624), a mail client (620), a mail server (622), a user interface (626), and the like. In some embodiments, computer system (600) may store user/application data (618), such as the data, variables, records, etc. as described in this invention. Such databases may be implemented as fault-tolerant, relational, scalable, secure databases such as Oracle or Sybase.

The operating system (628) may facilitate resource management and operation of the computer system (600). Examples of operating systems include, without limitation, Apple Macintosh™ OS X™, UNIX™, Unix-like system distributions (e.g., Berkeley Software Distribution (BSD), FreeBSD™, Net BSD™, Open BSD™, etc.), Linux distributions (e.g., Red Hat™, Ubuntu™, K-Ubuntu™, etc.), International Business Machines (IBM™) OS/2™, Microsoft Windows™ (XP™, Vista/7/8, etc.), Apple iOS™, Google Android™, Blackberry™ Operating System (OS), or the like. A user interface may facilitate display, execution, interaction, manipulation, or operation of program components through textual or graphical facilities. For example, user interfaces may provide computer interaction interface elements on a display system operatively connected to the computer system (600), such as cursors, icons, check boxes, menus, windows, widgets, etc. Graphical User Interfaces (GUIs) may be employed, including, without limitation, Apple™ Macintosh™ operating systems' Aqua™, IBM™ OS/2™, Microsoft™ Windows™ (e.g., Aero, Metro, etc.), Unix X-Windows™, web interface libraries (e.g., ActiveX, Java, JavaScript, AJAX, HTML, Adobe Flash, etc.), or the like.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., are non-transitory. Examples include random access memory (RAM), read-only memory (ROM), volatile memory, non-volatile memory, hard drives, CD ROMs, DVDs, flash drives, disks, and any other known physical storage media.

Finally, the language used in the specification has been principally selected for readability and instructional purposes, and it may not have been selected to delineate or circumscribe the inventive subject matter. Accordingly, the disclosure of the embodiments of the disclosure is intended to be illustrative, but not limiting, of the scope of the disclosure.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

The invention claimed is:

1. A method of predicting a risk of infection of a neonate by a neonate infection prediction system, the method comprising:

receiving health data of the neonate from a wearable health monitoring device and a monitoring system;

evaluating baseline input data comprising a plurality of baseline physiological parameters of the neonate based on the health data;

determining parameter values for baseline input data based on customized threshold data associated with each baseline physiological parameter, wherein the customized threshold data is determined using a customized threshold evaluation model;

evaluating a likelihood score based on the parameter values and predetermined weights; and predicting a risk of infection within the neonate based on one or more of the likelihood score and risk score.

2. The method as claimed in claim 1, wherein determining the customized threshold data using the customized threshold evaluation model comprising:

receiving low resolution data of the neonate from the monitoring system, wherein the low resolution data comprises demographic data associated with the neonate at the time of birth, and maternal medical related data as input;

receiving high resolution data captured by the wearable health monitoring device associated with the neonate at the time of birth, training data from a prediction database and medical reference data from a standards database, as input;

deriving baseline training data comprising at least one of time and frequency varying trends of baseline physiological parameters based on the high resolution data for training, wherein the plurality of baseline physiological parameters comprise heart rate variability, pleth variability index, core periphery temperature gradient, saturation variability, temperature gradient variability, perfusion index variability, and respiration rate variability;

generating a profile of each neonate based on the baseline training data; and determining the customized threshold data using the customized threshold evaluation model based on the neonate's profile, low resolution data and the medical reference data.

3. The method as claimed in claim 2, wherein determining the customized threshold data using the customized threshold evaluation model based on the neonate's profile, low resolution data and the medical reference data comprising:

estimating local threshold data for each baseline physiological parameter based on the baseline training data of the neonate;

estimating global threshold data for each baseline physiological parameter based on the low threshold data; and determining the customized threshold data for each baseline physiological parameter using the customized threshold evaluation model based on the local threshold data and the global threshold data associated with each baseline physiological parameter.

4. The method as claimed in claim 2, wherein the training data of each neonate comprises plurality of past values of likelihood scores of neonate infection for a plurality of neonates, past history of local threshold data, global threshold data, customized threshold data associated with each baseline parameter, a plurality of values and weights of the baseline physiological parameters corresponding to each of the plurality of likelihood scores, historical data of a plurality of risk prediction models associated with a plurality of neonate profiles, and a plurality of significant parameters associated with a plurality of neonate profiles and plurality of predicted values of risk scores and risk of infection-, wherein the health data of neonate comprises the low resolution data and the high resolution data measured at a current period of time to predict the risk of infection.

5. The method as claimed in claim 1, wherein determining parameter values for baseline input data based on customized threshold data associated with each baseline physiological parameter comprises:

comparing baseline input data with the customized threshold data; and determining parameter values for each baseline physiological parameter by determining a first value for a baseline physiological parameter if the baseline input data associated with the baseline physiological parameter exceeds the customized threshold data associated with the baseline physiological parameter; or determining a second value for the baseline physiological parameter if the baseline input data associated with the baseline physiological parameter is lesser than or equal to the customized threshold data associated with the baseline physiological parameter.

6. The method as claimed in claim 1, wherein predicting the risk of infection within the neonate based at least on the likelihood score comprising:

predicting that the neonate is more likely to have an infection if the likelihood score exceeds a likelihood threshold; and predicting that the neonate is less likely to have an infection if the likelihood score does not exceed the likelihood threshold.

7. The method as claimed in claim 2, wherein predicting the risk of infection within the neonate based on one or more of the likelihood score and risk score comprising:

selecting a risk prediction model based on the neonate's profile and the training data from the prediction database;

determining a plurality of significant parameters based on the neonate's profile and the training data, wherein the plurality of significant parameters indicate a set of parameters that are significant to predict the risk of infection within the neonate;

determining a risk score based on the selected risk prediction model and the plurality of significant parameters; and predicting the risk of infection based on the likelihood score and the risk score.

8. A system for predicting a risk of infection of a neonate, the system comprises:

a memory; and a processor that is communicably coupled to the memory, the processor is configured to:

receive health data of the neonate from a wearable health monitoring device and a monitoring system coupled to the processor;

evaluate baseline input data comprising a plurality of baseline physiological parameters of the neonate based on the health data;

determine parameter values for baseline input data based on customized threshold data associated with each baseline physiological parameter, wherein the customized threshold data is determined using a customized threshold evaluation model;

evaluate a likelihood score based on the parameter values and predetermined weights; and predict a risk of infection within the neonate based on one or more of the likelihood score and risk score.

9. The system as claimed in claim 8, wherein for determining the customized threshold data using the customized threshold evaluation model, the processor is configured to:

receive low resolution data of the neonate from the monitoring system, wherein the low resolution data comprises demographic data associated with the neonate at the time of birth, and maternal medical related data as input;

receive high resolution data captured by the wearable health monitoring device associated with the neonate at the time of birth, training data from a prediction database and medical reference data from a standards database, as input;

derive baseline training data comprising at least one of time and frequency varying trends of baseline physiological parameters based on the high resolution data for training, wherein the plurality of baseline physiological parameters comprise heart rate variability, pleth variability index, core periphery temperature gradient, saturation variability, temperature gradient variability, perfusion index variability, and respiration rate variability;

generate a profile of each neonate based on the baseline training data; and determine the customized threshold data using the customized threshold evaluation model based on the neonate's profile, low resolution data and the medical reference data.

10. The system as claimed in claim 9, wherein for determining the customized threshold data using the customized threshold evaluation model based on the neonate's profile, low resolution data and the medical reference data, the processor is configured to:

estimate local threshold data for each baseline physiological parameter based on the baseline training data of the neonate;

estimate global threshold data for each baseline physiological parameter based on the low threshold data; and determine the customized threshold data for each baseline physiological parameter using the customized threshold evaluation model based on the local threshold data and the global threshold data associated with each baseline physiological parameter.

11. The system as claimed in claim 9, wherein the training data of each neonate comprises plurality of past values of likelihood scores of neonate infection for a plurality of neonates, past history of local threshold data, global threshold data, customized threshold data associated with each baseline parameter, a plurality of values and weights of the baseline physiological parameters corresponding to each of the plurality of likelihood scores, historical data of a plurality of risk prediction models associated with a plurality of neonate profiles, and a plurality of significant parameters associated with a plurality of neonate profiles and plurality of predicted values of risk scores and risk of infection-, wherein the health data of neonate comprises the low resolution data and the high resolution data measured at a current period of time to predict the risk of infection.

12. The system as claimed in claim 8, wherein for determining parameter values for baseline input data based on customized threshold data associated with each baseline physiological parameter, the processor is configured to:

compare baseline input data with the customized threshold data; and determine parameter values for each baseline physiological parameter by:

determining a first value for a baseline physiological parameter if the baseline input data associated with the baseline physiological parameter exceeds the customized threshold data associated with the baseline physiological parameter; or determining a second value for the baseline physiological parameter if the baseline input data associated with the baseline physiological parameter is lesser than or equal to the customized threshold data associated with the baseline physiological parameter.

13. The system as claimed in claim 8, wherein for predicting the risk of infection within the neonate based at least on the likelihood score, the processor is configured to:

predict that the neonate is more likely to have an infection if the likelihood score exceeds a likelihood threshold; and predict that the neonate is less likely to have an infection if the likelihood score does not exceed the likelihood threshold.

14. The system as claimed in claim 9, wherein for predicting the risk of infection within the neonate based on one or more of the likelihood score and risk score, the processor is configured to:

select a risk prediction model based on the neonate's profile and the training data from the prediction database;

determine a plurality of significant parameters based on the neonate's profile and the training data, wherein the plurality of significant parameters indicate a set of parameters that are significant to predict the risk of infection within the neonate;

determine a risk score based on the selected risk prediction model and the plurality of significant parameters; and predict the risk of infection based on the likelihood score and the risk score.

15. A computer readable medium having instructions stored thereon, that in response to execution cause a computer to perform a method for predicting a risk of infection of a neonate, comprising:

receiving health data of the neonate from a wearable health monitoring device and a monitoring system;

evaluating baseline input data comprising a plurality of baseline physiological parameters of the neonate based on the health data;

determining parameter values for baseline input data based on customized threshold data associated with each baseline physiological parameter, wherein the customized threshold data is determined using a customized threshold evaluation model;

evaluating a likelihood score based on the parameter values and predetermined weights; and predicting a risk of infection within the neonate based on one or more of the likelihood score and risk score.

16. The computer readable medium as claimed in claim 15, wherein determining the customized threshold data using the customized threshold evaluation model comprising:

receiving low resolution data of the neonate from the monitoring system, wherein the low resolution data comprises demographic data associated with the neonate at the time of birth, and maternal medical related data as input;

receiving high resolution data captured by the wearable health monitoring device associated with the neonate at the time of birth, training data from a prediction database and medical reference data from a standards database, as input;

deriving baseline training data comprising at least one of time and frequency varying trends of baseline physiological parameters based on the high resolution data for training, wherein the plurality of baseline physiological parameters comprise heart rate variability, pleth variability index, core periphery temperature gradient, saturation variability, temperature gradient variability, perfusion index variability, and respiration rate variability;

generating a profile of each neonate based on the baseline training data; and determining the customized threshold data using the customized threshold evaluation model based on the neonate's profile, low resolution data and the medical reference data by:

estimating local threshold data for each baseline physiological parameter based on the baseline training data of the neonate;

estimating global threshold data for each baseline physiological parameter based on the low threshold data; and determining the customized threshold data for each baseline physiological parameter using the customized threshold evaluation model based on the local threshold data and the global threshold data associated with each baseline physiological parameter.

17. The computer readable medium as claimed in claim 16, wherein the training data of each neonate comprises plurality of past values of likelihood scores of neonate infection for a plurality of neonates, past history of local threshold data, global threshold data, customized threshold data associated with each baseline parameter, a plurality of values and weights of the baseline physiological parameters corresponding to each of the plurality of likelihood scores, historical data of a plurality of risk prediction models associated with a plurality of neonate profiles, and a plurality of significant parameters associated with a plurality of neonate profiles and plurality of predicted values of risk scores and risk of infection, wherein the health data of neonate comprises the low resolution data and the high resolution data measured at a current period of time to predict the risk of infection.

18. The computer readable medium as claimed in claim 15, wherein determining parameter values for baseline input data based on customized threshold data associated with each baseline physiological parameter comprises:

comparing baseline input data with the customized threshold data; and determining parameter values for each baseline physiological parameter by determining a first value for a baseline physiological parameter if the baseline input data associated with the baseline physiological parameter exceeds the customized threshold data associated with the baseline physiological parameter; or determining a second value for the baseline physiological parameter if the baseline input data associated with the baseline physiological parameter is lesser than or equal to the customized threshold data associated with the baseline physiological parameter.

19. The computer readable medium as claimed in claim 15, wherein predicting the risk of infection within the neonate based at least on the likelihood score comprising:

predicting that the neonate is more likely to have an infection if the likelihood score exceeds a likelihood threshold; and predicting that the neonate is less likely to have an infection if the likelihood score does not exceed the likelihood threshold.

20. The computer readable medium as claimed in claim 16, wherein predicting the risk of infection within the neonate based on one or more of the likelihood score and risk score comprising:

selecting a risk prediction model based on the neonate's profile and the training data from the prediction database;

determining a plurality of significant parameters based on the neonate's profile and the training data, wherein the plurality of significant parameters indicate a set of parameters that are significant to predict the risk of infection within the neonate;

determining a risk score based on the selected risk prediction model and the plurality of significant parameters; and predicting the risk of infection based on the likelihood score and the risk score.

* * * * *